United States Patent [19]

Squire

[11] 4,393,227

[45] Jul. 12, 1983

[54] PROCESS FOR DECHLORINATING ORGANIC COMPOUNDS

[75] Inventor: Edward N. Squire, Glen Mills, Pa.

[73] Assignee: E. I. Du Pont de Nemours and Company, Wilmington, Del.

[21] Appl. No.: 292,060

[22] Filed: Aug. 12, 1981

[51] Int. Cl.$^3$ .......................................... C07D 317/10
[52] U.S. Cl. .................................. 549/455; 570/135; 570/136
[58] Field of Search .................. 260/340.9 R; 549/455

[56] References Cited

U.S. PATENT DOCUMENTS 2,918,478  12/1959  Newman ..................... 260/340.9 R
3,865,845  2/1975  Resnick ............................. 260/340.9

FOREIGN PATENT DOCUMENTS 1170934  5/1964  Fed. Rep. of Germany.

OTHER PUBLICATIONS

Chem. Abstracts 61:5516a (1964).

Primary Examiner—Ethel G. Love

[57] ABSTRACT

Olefinic compounds are made from their vicinally chlorinated organic precursors by dechlorination with metallic magnesium in the presence of a mercury-based promoter, which may be a water-soluble mercury salt or metallic mercury, and of a catalytic amount of iodine. This process is particularly suitable for dechlorinating 4,5-dichloro-dioxolanes to the corresponding dioxoles. 4,5-Difluoro-2,2 bis(trifluoromethyl)-1,3-dioxole, which can be made by this process in a reproducible manner from 4,5-dichloro-4,5-difluoro-2,2-bis(trifluoromethyl)-1,3-dioxolane, is a useful monomer for making amorphous homopolymers and copolymers with tetrafluoroethylene, which are well suited for wire coating, finishes, and transparent glazing for corrosive service.

18 Claims, No Drawings

PROCESS FOR DECHLORINATING ORGANIC COMPOUNDS

BACKGROUND OF THE INVENTION

This invention relates to a process for making olefinic organic compounds by removing two vicinal chlorine atoms from the corresponding dichloro or polychloro compounds.

Olefinic organic compounds are characterized by the presence of a carbon-carbon double bond $>C=C<$. They are normally made by dechlorination of vicinal dichloro compounds with metallic zinc or magnesium. While this technique gives satisfactory results in most cases, it sometimes is unreliable or gives low yields, especially where the starting dichloro compound also carries a fluorine atom on one of the vicinal chlorine-carrying carbon atoms. A case in point is the dechlorination of 4,5-dichloro-4,5-difluoro-2,2-bis(trifluoromethyl)-1,3-dioxolane (1) to 4,5-difluoro-2,2-bis(trifluoromethyl)-1,3-dioxole (2), as shown in the following equation (A):

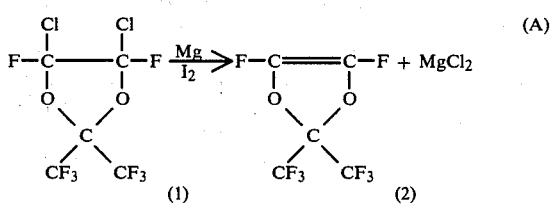

This reaction, described in U.S. Pat. No. 3,865,845 to Resnick, is erratic; the desired product is in some runs obtained in satisfactory yields, while in other runs it is obtained either in low yields or not at all.

It thus is desirable to provide a reliable and reproducible process for effecting such dechlorinations in good yields.

SUMMARY OF THE INVENTION

According to the present invention, there is now provided a process for dechlorinating an organic compound having vicinal chlorine atoms to an ethylenically unsaturated compound, said process comprising contacting the organic chlorine-containing compound with at least a stoichiometric amount of metallic magnesium, a mercury-based promoter selected from water-soluble mercury salts and metallic mercury, and iodine in the presence of tetrahydrofuran;
with the proviso that:
instead of magnesium and the mercury-based promoter, one can use magnesium amalgam.

DETAILED DESCRIPTION OF THE INVENTION

The process of this invention is particularly valuable for the dechlorination of chlorofluoro compounds, for example as shown in the following equation (B):

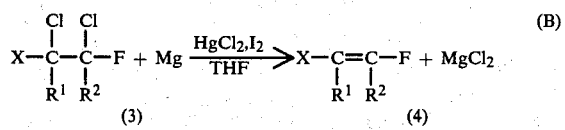

where X is an organic radical, a chlorine or fluorine atom, or hydrogen; and each of $R^1$ and $R^2$ independently is an organic radical, or both $R^1$ and $R^2$ taken together form a divalent organic radical. An organic radical for the purpose of the above definitions may be substituted or unsubstituted and may contain heteroatoms.

The dechlorination reaction for which this process is particularly recommended is the preparation of dioxoles from dioxolanes as follows:

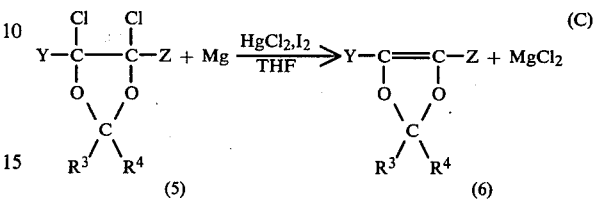

where each of Y and Z independently is hydrogen, chlorine, or fluorine; and each of $R^3$ and $R^4$ independently is hydrogen, fluorine, or trifluoromethyl.

In all the above equations (A), (B) and (C) the graphic representation of compounds (1) through (6) is merely schematic and is not intended to imply any spatial or geometric configurations. THF stands for tetrahydrofuran.

Water-soluble mercury salts will be principally mercuric salts such as mercuric acetate, chloride, and nitrate; and mercurous nitrate. While equations (B) and (C) show the use of mercuric chloride, the other salts can be used in its stead. Preferably, the weight ratio of magnesium to mercury salt is 1:0.01 to 1:0.15. When metallic mercury is used, the Mg/Hg weight ratio may be about 100:1 to 0.2:1. Magnesium amalgam may be prepared in advance in the same Mg/Hg ratios. The weight ratio of magnesium to iodine is about 1:0.75 to 1:0.0002.

Representative chlorine-containing compounds which can be dechlorinated by the process of this invention to the corresponding ethylenically unsaturated compounds include, for example, the following:

1,2-dichlorobutane; 1,2-dichlorocyclohexane; 3,4-dichloro-2-methylpentane; 3,4-dichloro-4-fluorohexane, 1,2-dichlorotrifluoroethyl pentafluoroethyl ether; 4,5,5-trichloro-2,2,4-trifluoro-1,3-dioxolane; 4,5-dichloro-4,5-difluoro-2,2-bis(trifluoromethyl)-1,3-dioxolane; 4,4,5,5-tetrachloro-2,2-bis(trifluoromethyl)-dioxolane; 4,5-dichloro-2,2,4,5-tetrafluoro-1,3-dioxolane; and 4,4,5-trichloro-5-fluoro-2,2-bis(trifluoromethyl)-1,3-dioxolane.

The amount of tetrahydrofuran (THF) normally should be sufficient to effectively absorb and dissipate the heat of the reaction. Preferably, the volume of THF should be larger than that of the chlorine-containing starting material. The dechlorination is conducted the most efficiently by continuously introducing the chlorine-containing compound and distilling off the ethylenically unsaturated product as quickly as it is formed together with a portion of THF and some unchanged starting material. The product thus is removed prior the complete conversion. Often, when the product is distilled off after complete conversion has taken place, the actual yield of ethylenically unsaturated product is lower. The volume ratio of THF to the starting chlorine-containing compound can be as high as 50:1 or even higher, but a ratio of (10–30):1 and particularly (2–20):1 is preferred. When dioxole is made from a 4,5-dichloro dioxolane, it is preferred to distill the product at a higher rate than the rate of addition of the dioxolane to the reaction medium. This results in higher yields. Typically, the ratio of volume of liquid distilled, mL/min, to weight of dioxolane added, g/min, is about 1.1–10, preferably 1.5–8, and especially 1.5–5 mL/g.

The removal of higher boiling dechlorination products can be assisted by the addition of high boiling, inert, organic liquids such as, for example, benzonitrile or diglyme.

Preferably, an excess of magnesium is employed in this reaction, and the preferred amount of magnesium is 1.1–8 gram-atoms of magnesium per two gram-atoms of vicinal chlorine to be removed. The particularly preferred amount of magnesium is 2–6 gram-atoms per two gram-atoms of chlorine.

The ratios of magnesium to mercury-based promoter and to iodine are important to the reproducibility and reliability of the dechlorination reaction. The particularly preferred weight ratio of magnesium to mercuric salt is within the range of 1:0.01 to 1:0.07 and especially 1:0.02 to 1:0.04, while the preferred weight ratio of magnesium to iodine is within the range of 1:0.35 to 1:0.01 and especially 1:0.07 to 1:0.05.

This invention is now illustrated by representative examples, where all parts, proportions, and percentages are by weight unless otherwise stated. All non-SI data have been converted to SI units.

EXAMPLE 1

A 100-mL 3-neck, round bottom, borosilicate flask equipped with a magnetic stirrer, thermometer, syringe needle insert, Vigreux still column topped with a still head cooled by a dry ice condenser leading to a receiver and trap, both immersed in dry ice and under 101 kPa of nitrogen, was charged with 3.6 g of magnesium turnings, 0.5 g of iodine and 30 mL of tetrahydrofuran.

The stirred mixture was heated to 66° C. Time was allowed for the iodine to react with the magnesium; this reaction is evidenced by the disappearance of the iodine color in the solution. Following the decolorization, 9.6 g of 4,5-dichloro-4,5-difluoro-2,2-bis(trifluoromethyl)-1,3-dioxolane was slowly added to the reaction flask; there was no reaction. The flask contents were heated for an additional two hours at 66° C. with stirring; there still was no evidence of a reaction; an exothermic reaction did not occur and analyses of small amounts of the head contents did not show the presence of 4,5-difluoro-2,2-bis(trifluoromethyl)-1,3-dioxole, or perfluoro(2,2-dimethyl-1,3-dioxole) (PDD), only the starting dioxolane and tetrahydrofuran.

The reaction mixture was then allowed to cool to room temperature and, after standing overnight, 0.5 g of mercuric chloride was added. The mixture was stirred at room temperature for 10 minutes and then heated; after heating for 20 minutes, a violent reaction occurred necessitating cooling the reaction vessel in a dry ice/acetone bath. Normal distillation was then carried out for an hour. The distillate was extracted with water to remove some tetrahydrofuran and 2.8 g (38% yield) of PDD was obtained. This dioxole is a useful monomer for homopolymerizing or copolymerizing with tetrafluoroethylene to amorphous polymeric materials suitable, among others, for wire coating, finishes, and transparent glazing for corrosive service.

EXAMPLE 2

The equipment was the same as in Example 1 except that a 300 mL flask was used. Also, the amounts of ingredients were greater; 7.3 g of magnesium turnings, 0.2 g of mercuric chloride, 0.1 g of iodine, 80 mL of tetrahydrofuran and 18.9 g of 4,5-dichloro-4,5-difluoro-2,2-bis(trifluoromethyl)-1,3-dioxolane.

The flask contents were warmed up to 66° C. over a 25 minute period, during which time the iodine and mercuric chloride reacted with the magnesium. Slow addition of the dioxolane was started and continued for seventy minutes. Twenty minutes after the start of the addition, distillation began and continued for 102 minutes to produce 15 mL of distillate. Water extraction of the distillate followed by gas chromatographic analysis showed that 7.4 g (50% yield at 99% conversion) of PDD had been produced. The ratio of distillate (mL) to starting dioxolane (g) was 15/102:18.9/70=0.147/0.27=0.54.

EXAMPLE 3

The same equipment was employed as in Example 1 but different quantities of ingredients were used: 3.6 g of magnesium turnings, 0.2 g of mercuric chloride, 0.1 g of iodine, 40 mL of tetrahydrofuran, and 6.3 g of 4,5-dichloro-4,5-difluoro-2,2-bis(trifluoromethyl)-1,3-dioxolane.

The flask contents were heated to reflux and the iodine color of the solution disappeared. After holding at reflux for 3 minutes, addition of the dioxolane was started. After another 5 minutes the distillation was commenced. The dioxolane addition was complete after 42 minutes, and the distillation was stopped in 37 minutes, after 11.5 mL had distilled. The rate of distillation was 11.5 mL/37 minutes=0.31 mL/minute, and the rate of addition was 6.3 g/42 minutes=0.15 g/minute. The ratio of distillation to addition rates was 0.31/0.15=2.07 mL/g.

The distillate was extracted with water to remove the tetrahydrofuran and the product analyzed by gas chromatography; this showed a PDD yield of 77.3% at 77.5% conversion.

EXAMPLE 4

Magnesium turnings, 12.1 g, were dry stirred for 10 minutes with 0.2 g of metallic mercury in a 300 mL, 3-neck, round bottom flask equipped as described in Example 2. The flask was then charged with 0.2 g of iodine and 80 mL of THF; the same type of still was used as in Example 2 except that the head was water-cooled. The procedure of Example 2 was followed and 31.5 g of 2,2-bis(trifluoromethyl)-4,5-dichloro-4,5-difluoro-1,3-dioxolane was introduced into the flask at 0.24 mL/min; the addition was completed in 141 minutes. Distillation was commenced 10 minutes after the start of the addition and continued until 15 mL of distillate containing PDD was obtained. The distillate was then extractively distilled with water to remove the THF. PDD obtained in this way had a purity of over 99.4% as measured by gas chromatography and infrared spectroscopy.

EXAMPLE 5

Magnesium turnings, 3.6 g, were mixed with 1 g of metallic mercury in a vial and shaken overnight in air at room temperature on a wrist action shaker to form an amalgam. Following the method of Example 1, the flask was charged with this magnesium amalgam, 0.2 of iodine and 30 mL of tetrahydrofuran. After heating to 63° C. over a 26 minute period, the addition of the 4,5-dichloro-4,5-difluoro-2,2-bis(trifluoromethyl)-1,3-dioxolane was started at 0.09 mL/min. Within 19 minutes the color of the solution darkened, which indicated that dechlorination had begun. After additional 15 minutes, during which time the still head temperature dropped from 63° C. to 37° C., distillation of the PDD product (b.p. 33° C.) and tetrahydrofuran (b.p. 67° C.) mixture was started. The slow distillation was carried out at head temperatures ranging from 35° to 65° C. The tetrahydrofuran was extracted with water from the PDD, which was identified by its characteristic infrared absorbancies.

EXAMPLE 6

PDD was also produced in an identical manner as in Example 5 when an amalgam consisting of 3.6 g of magnesium and 10 g of mercury was employed in the reaction. The only noticeable difference between this and Example 5 was that a longer induction time was required when the larger amount of mercury was employed.

I claim:

1. A process for dechlorinating an organic compound selected from the group consisting of

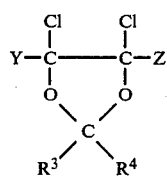

where each of Y and Z independently is hydrogen, chlorine or fluorine, provided at least one of Y and Z is fluorine; and each of $R^3$ and $R^4$ independently is hydrogen, fluorine or trifluoromethyl to the ethylenically unsaturated compound, said process comprising contacting the organic chlorine-containing compound with at least a stoichiometric amount of metallic magnesium, a mercury based promoter selected from water-soluble mercury salts and metallic mercury, and iodine in the presence of tetrahydrofuran at a temperature from about room temperature to at least the boiling point of tetrahydrofuran at the operating pressure;

with a proviso that magnesium amalgam can be used in lieu of magnesium and the mercury-based promoter.

2. The process of claim 1 wherein each of Y and Z is fluorine, and each of $R^3$ and $R^4$ is trifluoromethyl.

3. The process of claim 1 wherein each of Y and Z is hydrogen, and each of $R^3$ and $R^4$ is trifluoromethyl or fluorine.

4. The process of claim 1 wherein each of Y, Z, $R^3$ and $R^4$ is fluorine.

5. The process of claim 1 wherein Y is hydrogen; Z is fluorine; and each of $R^3$ and $R^4$ fluorine or trifluoromethyl.

6. The process of claim 1 wherein Y is chlorine; Z is fluorine; and each of $R^3$ and $R^4$ is trifluoromethyl or fluorine.

7. The process of claim 1 wherein the starting dioxolane is added gradually over a suitable period to a hot reaction medium consisting of tetrahydrofuran, magnesium, mercuric chloride, and iodine, and liquid is distilled from the reaction medium at such a rate that its volume, in milliliters, is greater than the amount of the starting dioxolane, in grams, added during the same period.

8. The process of claim 7 wherein the ratio of the volume of liquid recovered by distillation, in mL/min, to the weight of dioxolane added, in g/min, is about 1.1–10.

9. The process of claim 8 wherein the ratio is about 1.5–8 mL/g.

10. The process of claim 9 wherein the ratio is about 1.5–5 mL/g.

11. The process of claim 1 wherein the amount of magnesium is 1.1–8 gram-atoms per two gram-atoms of vicinal chlorine to be removed.

12. The process of claim 10 wherein the amount of magnesium is 2–6 gram-atoms per two gram-atoms of vicinal chlorine.

13. The process of claim 1 wherein the water-soluble mercury salt is selected from mercuric nitrate, mercuric chloride, mercuric acetate, and mercurous nitrate.

14. The process of claim 13 wherein the weight ratio of magnesium to mercury salt is 1:0.01 to 1:0.15, and the weight ratio of magnesium to iodine is 1:0.75 to 1:0.002.

15. The process of claim 14 wherein the mercury salt is a mercuric salt, and the weight ratio of magnesium to mercuric salt is 1:0.01 to 1:0.07, and the weight ratio of magnesium to iodine is 1:0.35 to 1:0.01.

16. The process of claim 15 wherein the weight ratio of magnesium to mercuric salt is 1:0.02 to 1:0.04, and the weight ratio of magnesium to iodine is 1:0.07 to 1:0.05.

17. The process of claim 1 wherein the mercury-based promoter is metallic mercury, and the weight ratio of magnesium to mercury is about 100:1 to 0.2:1.

18. A process of claim 1 which is carried out at atmospheric pressure within the temperature range of room temperature to the boiling temperature of tetrahydrofuran.

* * * * *